US005744330A

United States Patent [19]
Domingues

[11] Patent Number: 5,744,330
[45] Date of Patent: Apr. 28, 1998

[54] CATABOLITE NON-REPRESSED SUBSTRATE-LIMITED YEAST STRAINS

[75] Inventor: David J. Domingues, Plymouth, Minn.

[73] Assignee: The Pillsbury Company, Minneapolis, Minn.

[21] Appl. No.: 436,979

[22] Filed: May 8, 1995

Related U.S. Application Data

[60] Division of Ser. No. 335,685, Nov. 8, 1994, Pat. No. 5,508,047, which is a continuation-in-part of Ser. No. 144,236, Oct. 27, 1993, Pat. No. 5,494,686, which is a continuation-in-part of Ser. No. 829,453, Jan. 31, 1992, abandoned, said Ser. No. 335,685, is a continuation-in-part of Ser. No. 87,616, Jul. 2, 1993, Pat. No. 5,492,702, which is a continuation-in-part of Ser. No. 26,927, Mar. 5, 1993, abandoned.

[51] Int. Cl.$^6$ .................... C12P 19/02; C12P 7/06
[52] U.S. Cl. .................. 435/105; 426/8; 435/101; 435/255.2; 435/942
[58] Field of Search .................... 435/161, 942, 435/105, 255.2

[56] References Cited

U.S. PATENT DOCUMENTS 5,047,340   9/1991   Dickson .................... 435/161

OTHER PUBLICATIONS

"Carbon and Phosphate Utilization", M. Johnston and M. Carlson, in The Moleular and Cellular Biology of the Yeast Saccharomyces, 1992, pp. 200–210.

"Induction of Galactokinase in Saccharomyces cerevisiae: Kinetics of Induction and Glucose Effects", B. Adams, Journal of Bacteriology, Aug. 1972, vol. 111, No. 2, pp. 308–315.

"Catabolite Repression", Boris Magasanik, Cold Spring Harbor Symp. Quant. Biol. 26, pp. 249–256.

*Primary Examiner*—Herbert J. Lilling
*Attorney, Agent, or Firm*—Janal M. Kalis; Aleya Rahman

[57] ABSTRACT

The present invention includes a yeast cell utilizing solely galactose as a carbohydrate source in the presence of glucose.

4 Claims, 8 Drawing Sheets

CATABOLITE NON-REPRESSED SUBSTRATE-LIMITED YEAST STRAINS

This application is a divisional of application Ser. No. 08/335,685 filed on Nov. 8, 1994, now U.S. Pat. No. 5,508,047, which is a Continuation-in-Part of U.S. application Ser. No. 08/144,236 filed Oct. 27, 1993, now U.S. Pat. No. 5,494,686, which is a Continuation-in-Part of U.S. application Ser. No. 07/829,453, filed Jan. 31, 1992, now abandoned. U.S. application Ser. No. 08/335,685 is also a Continuation-in-Part of U.S. application Ser. No. 08/087,616, filed Jul. 2, 1993, now U.S. Pat. No. 5,492,702, which is a Continuation-in-Part of U.S. application Ser. No. 08/026,927, filed Mar. 5, 1993, now abandoned.

BACKGROUND OF THE INVENTION

The present invention relates to a yeast cell utilizing solely galactose as a carbohydrate source in a presence of glucose.

Conventional yeast cells have activatable enzymes that enable the yeast cells to metabolize a variety of sugars. The sugars include glucose, maltose and galactose. Regulation of activities of the enzymes is based upon a selective activation and suppression of enzyme activity. The activities of enzymes aiding in metabolism of sugars other than glucose are suppressed when the yeast cell is grown in a media that includes glucose as a carbohydrate source for the yeast cell.

The suppression in enzyme activity occurs by one of two mechanisms. A first mechanism, glucose inactivation, rapidly inhibits the function of some enzymes and other proteins by modification and/or degradation of the proteins. A second mechanism, glucose repression, reduces the expression of many genes making enzymes and regulating enzyme activity at a transcriptional level.

Glucose repression in yeast cells is similar to a metabolic process termed "catabolite repression" in the organism, *Escherichia coli*. The term "catabolite repression" reflects a belief that repression of gene transcription is caused not so much by glucose itself but by glucose catabolites, as described by B. Magasanic in "Catabolite repression," in *Cold Spring Harbor Symp, Quant. Biol.* 26: 249 (1962). In the present application, the term "glucose repression" is used interchangeably with "catabolite repression".

The expression of a large number of yeast cell genes is subject to glucose repression. However, the degree of glucose repression varies from gene to gene. For example, expression of genes involved in galactose utilization, galactose genes (GAL genes), is repressed at least 1000-fold by glucose. Expression of genes involved in maltose metabolism, maltose genes, is repressed by about 15 fold as described by M. Johnston et al. in *The Molecular and Cellular Biology of the Yeast Saccharomyces* (1992) at 226.

Glucose appears to have two effects on expression of GAL genes. The first effect is that an addition of glucose to a galactose-based substrate media causes a yeast culture growing on the galactose enriched media to display a nearly complete but transient repression of GAL gene expression. The second effect is that GAL enzyme synthesis subsequently resumes at a reduced rate as described by Adams in an article, "Identification of glucokinase in *Saccharomyces cerevisiae*: Kinetics of induction and glucose effects," *J. Bacteriol III*: 308 (1972).

Because of glucose repression, conventional yeast cultures grow on glucose in three phases in a batch culture as described by E. Jones, et al. in *The Molecular and Cellular Biology of the Yeast Saccharomyces* (1992). In a first or rapid phase of growth, glucose is fermented with a concomitant glucose repression of gene expression. Shortly before the glucose is depleted, the culture enters a second growth phase during which glucose-repressed genes become de-repressed, adapting the culture for subsequent oxidation of an ethanol metabolite that accumulates during glucose utilization. De-repression of the synthesis of some enzymes begins well before glucose exhaustion and reaches maximal levels during growth on ethanol. Growth in a third or last phase is slow and ceases with the exhaustion of the available ethanol.

Because of a great adaptability and versatility of yeast strains generally, predicting performance of a particular yeast strain when the yeast strain is exposed to a complex nutrient substrate has been exceedingly difficult. On one hand, although a yeast strain might have a preference for a carbohydrate such as galactose, the yeast strain preference for galactose is undermined when the yeast is exposed to a substrate having a concentration of glucose. The mere presence of glucose tends to repress galactose metabolism. The yeast strain may be prevented from utilizing any carbohydrate at all. Alternatively, the yeast strain may revert to glucose metabolism.

SUMMARY OF THE INVENTION

The present invention includes a yeast cell of the genus species *Saccharomyces cerevisiae* that is capable of utilizing solely galactose as a carbohydrate source in a presence of glucose. The present invention also includes a yeast cell having a tolerance for ethanol of a concentration of at least about 6% by weight in a nutrient matrix. The present invention further includes a yeast cell that is substantially free of enzyme activity of proteinase A and proteinase B and carboxypeptidase Y.

DETAILED DESCRIPTION OF THE PREFERRED EMBODIMENTS

Figure 1:
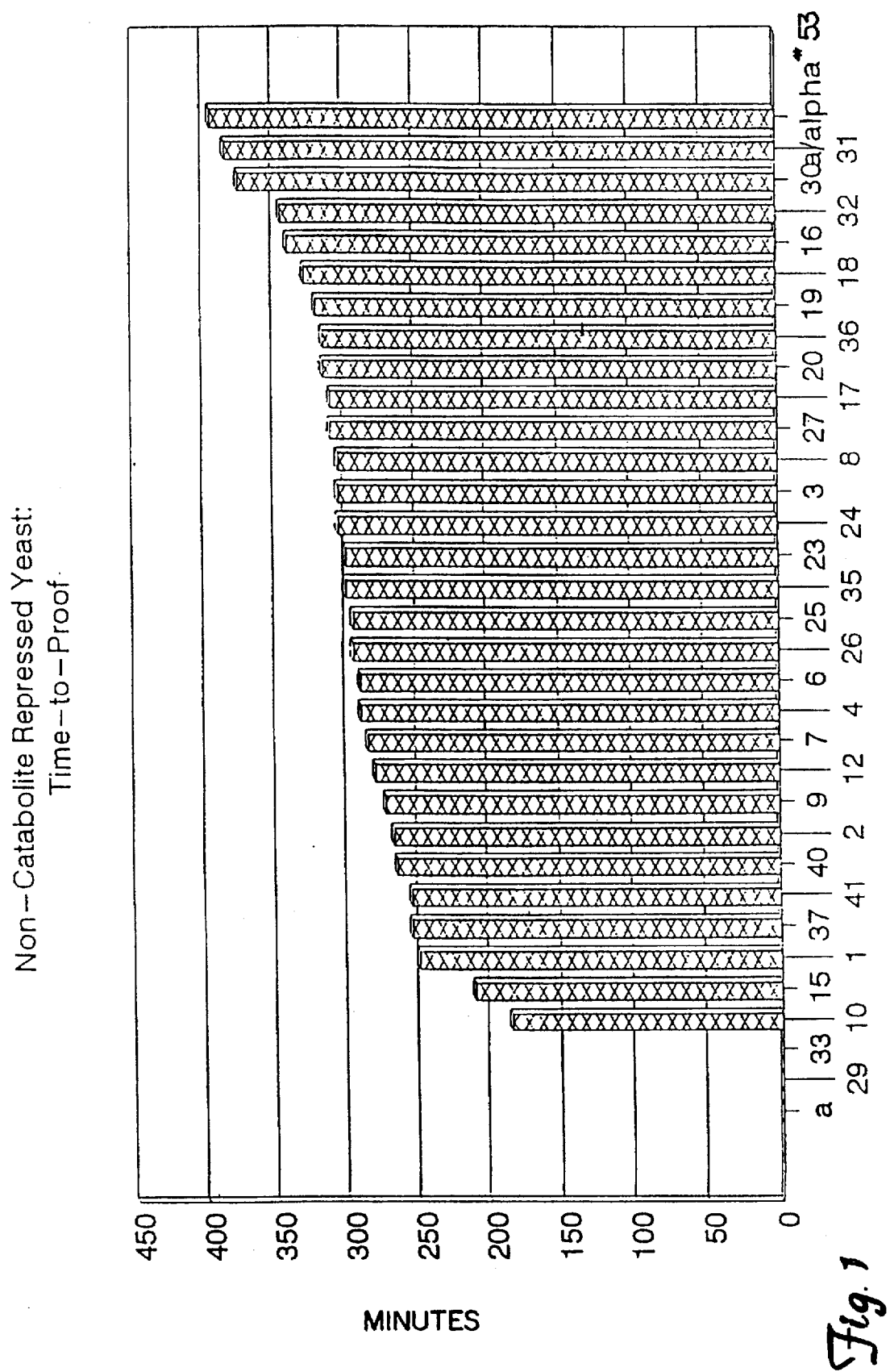
FIG. 1 graphically shows bread dough proof times for candidate catabolite non-repressed, CAT-, haploid yeast strains.
Figure 2:
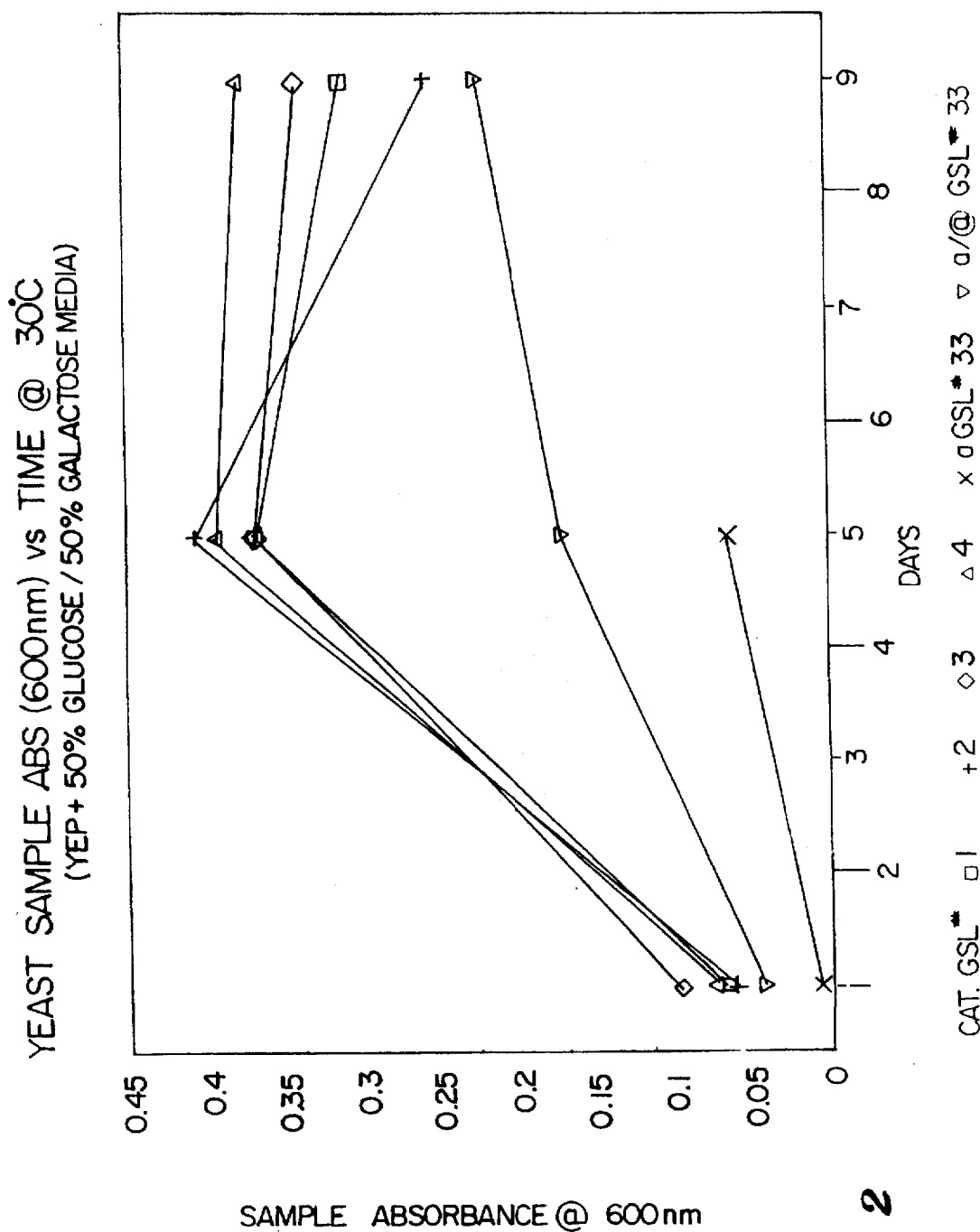
FIG. 2 graphically shows growth rates for CAT- glucose substrate limited, GSL, strains 1, 2, 3 and 4 and non CAT-control strains as measured by absorbance at 600 nanometers, nm, of a culture of each yeast strain.
Figure 3:
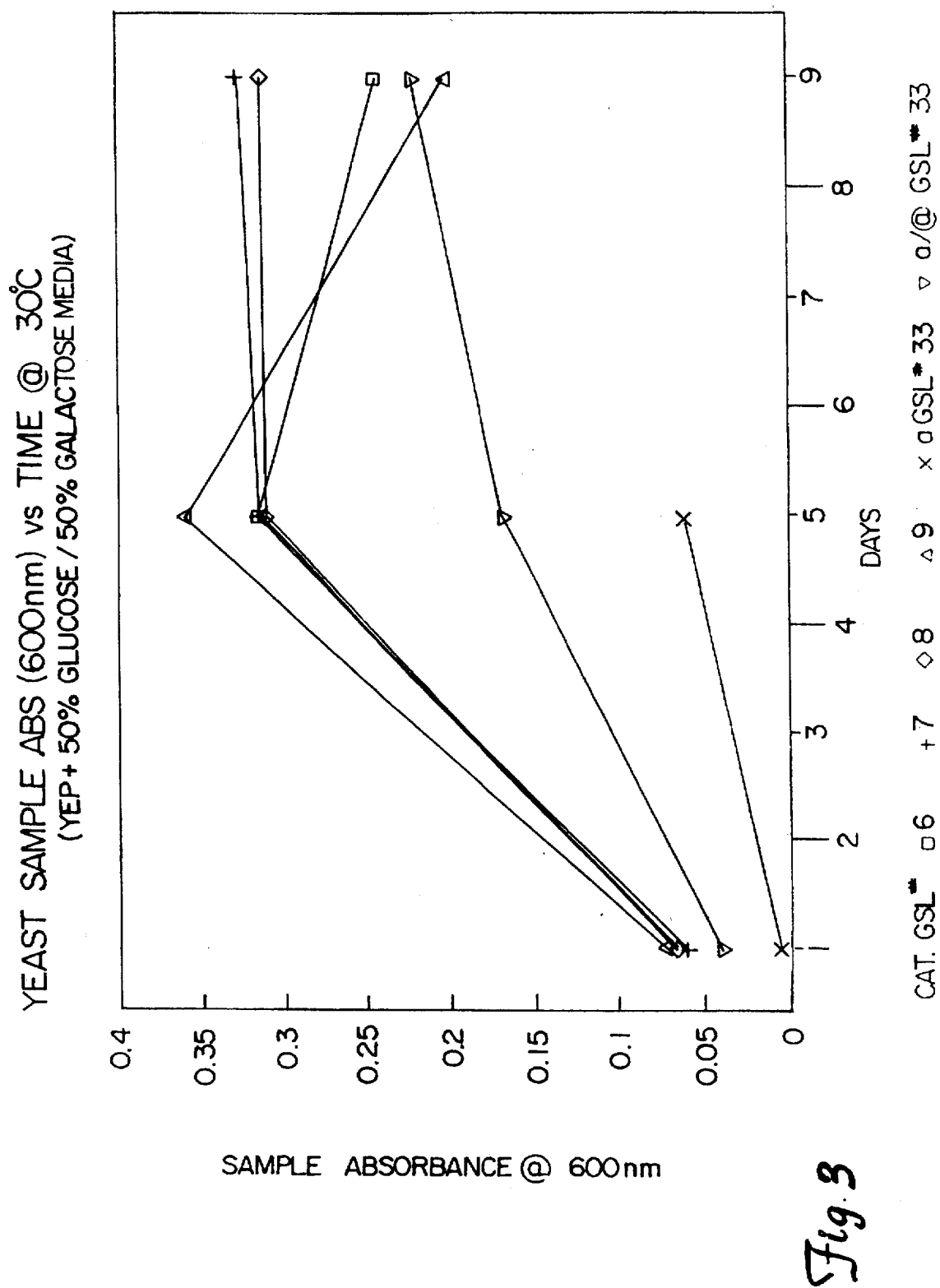
FIG. 3 graphically shows growth rates for CAT- GSL strains 6, 7, 8 and 9 and control strains as measured by absorbance at 600 nm of a culture of each yeast strain.
Figure 4:
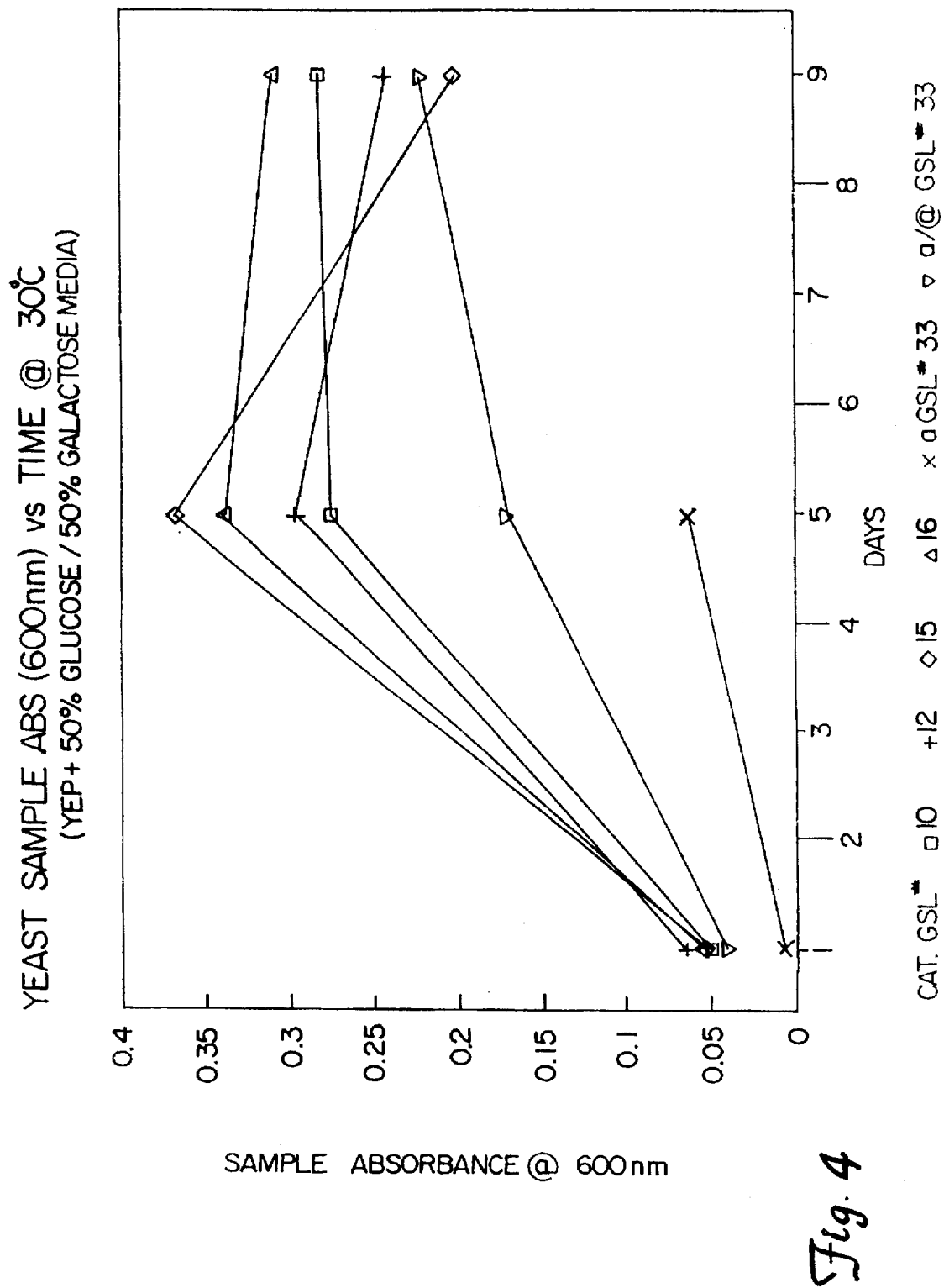
FIG. 4 graphically shows growth rates for CAT- GSL strains 10, 12, 15 and 16 and control strains as measured by absorbance at 600 nm of a culture of each yeast strain.
Figure 5:
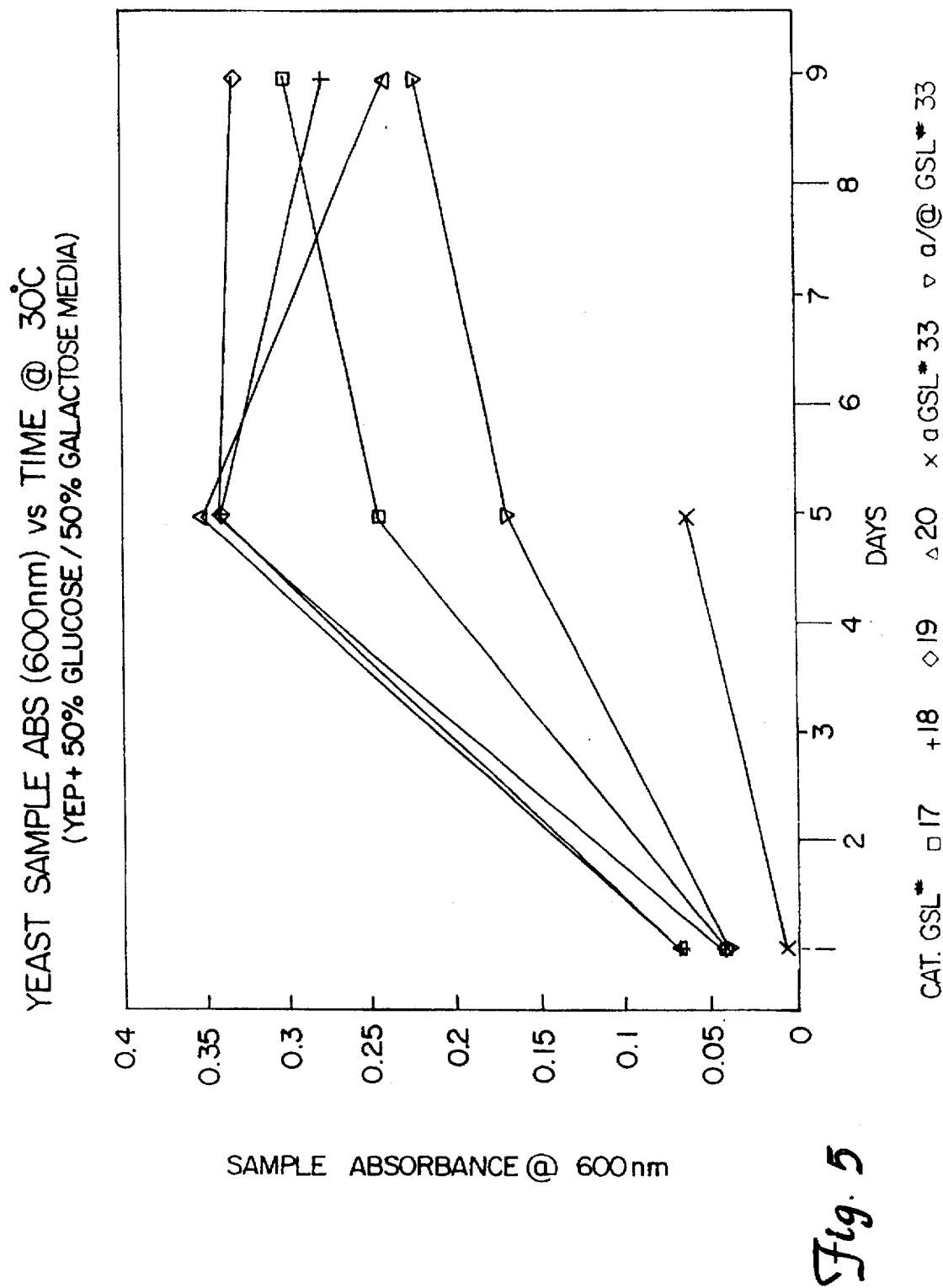
FIG. 5 graphically shows growth rates for CAT- GSL strains 17, 18, 19 and 20 and control strains as measured by absorbance at 600 nm of a culture of each yeast strain.
Figure 6:
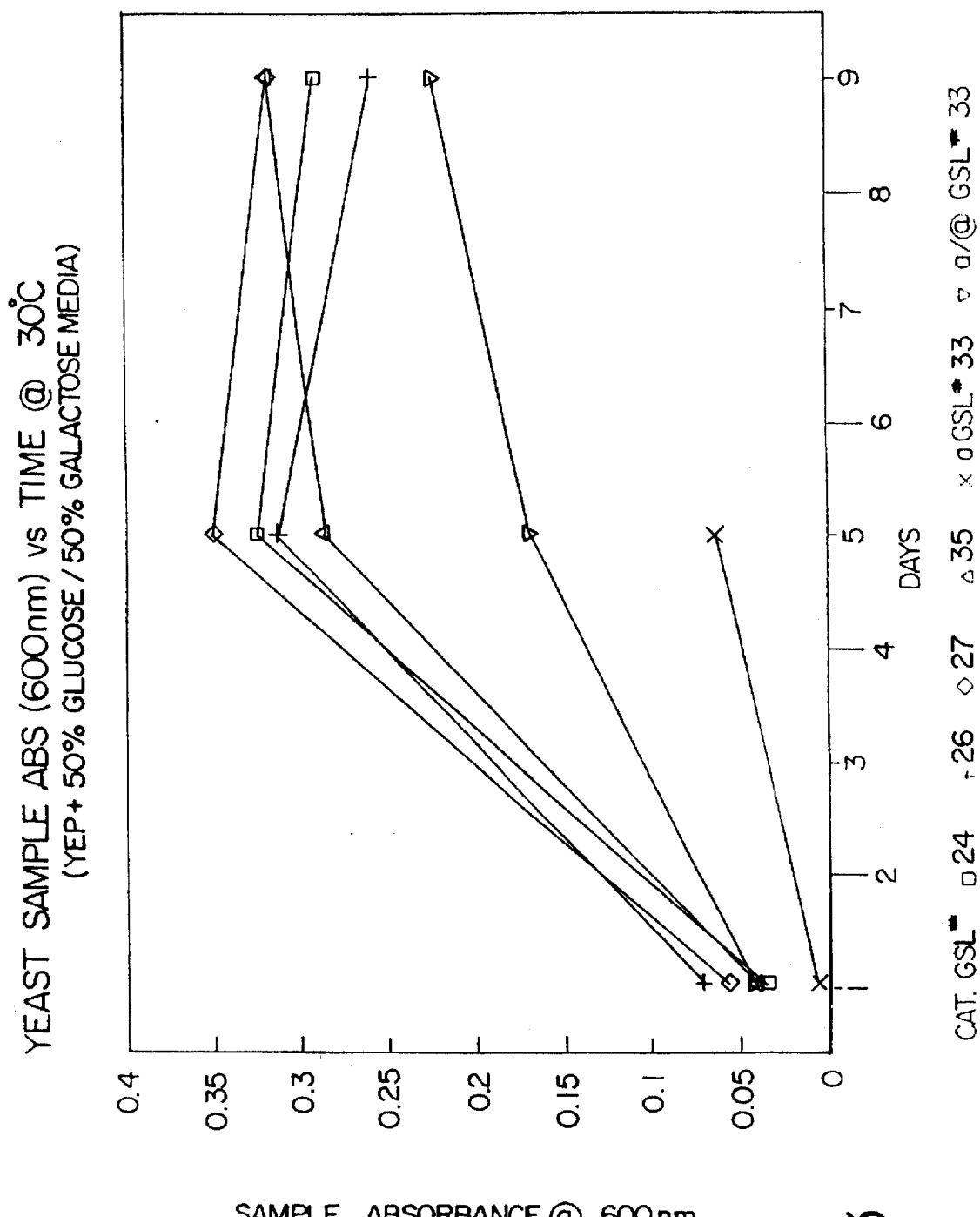
FIG. 6 graphically shows growth rates for CAT- GSL strains 24, 23, 27 and 35 and control strains as measured by absorbance at 600 nm of a culture of each yeast strain.
Figure 7:
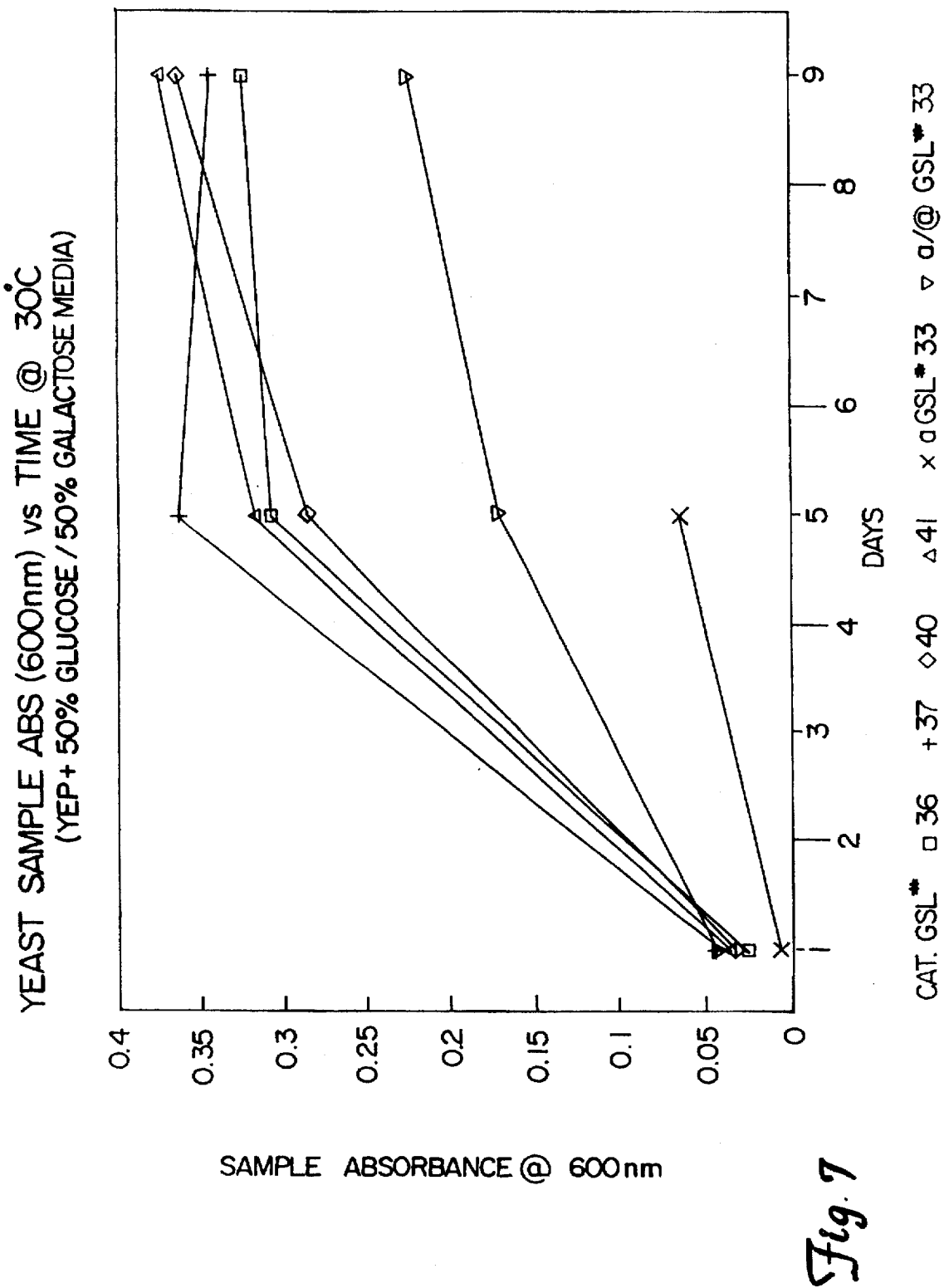
FIG. 7 graphically shows growth rates for CAT- GSL strains 36, 37, 40 and 41 and control strains as measured by absorbance at 600 nm of a culture of each yeast strain.

The present invention includes a diploid yeast cell of the genus species *Saccharomyces cerevisiae* utilizing solely galactose as a carbohydrate source in a presence of glucose. A nutrient matrix such as bread dough made with the yeast strain of the present invention can be controllably proofed within a time that is about one-half the time required for proofing bread doughs made with a galactose substrate limited yeast (hereinafter sometimes referred to as. GSL yeast or GAL-substrate limited yeast.) The ability to controllably proof a dough is especially important when the dough is packed in a closed container such as a paperboard can. In one embodiment, the galactose utilizing yeast strain of the present invention also has a tolerance for ethanol that is greater than ethanol tolerance of GSL yeast.

The galactose utilizing yeast cell has a use in leavening and proofing bread dough, particularly refrigeratable bread dough. The ethanol tolerance feature of the yeast also reduces proof time of bread dough made with the yeast.

The galactose utilizing yeast cell also has use in food waste processing. Cheese production generates a large quantity of whey, which is substantially lactose and water. Conventional processing uses yeast, enzymes and/or acid to hydrolyze the lactose to glucose and galactose, which are further metabolized by yeast to ethanol. In some instances, yeast that can be used to hydrolyze the lactose do not efficiently metabolize the resultant glucose or galactose, so several different types of yeast may be used to break down lactose completely into ethanol. Conventional yeast cells preferentially ferment glucose over galactose. Consequently, galactose is a secondary end product of the process. The yeast cells of the present invention can be used to selectively convert galactose into ethanol, leaving glucose untouched, or can be used in combination with conventional strains of bacteria to convert glucose and galactose simultaneously to ethanol.

In one other embodiment, the yeast cell of the present invention further includes a proteinase activity that is diminished as compared to a conventional yeast cell. The proteinase activity is diminished because the yeast cell is substantially free of activity of proteinase A, proteinase B and carboxypeptidase Y. The elimination of these enzyme activities has resulted in a 90% reduction in post-lysis proteolytic activity as compared to a conventional yeast cell. This feature of the yeast cell renders the yeast cell more suitable to a use such as leavening and proofing a refrigeratable or freezable dough.

The proteinases degrade a gluten matrix in bread dough structure that results in an overall breakdown of the dough into a fluid, syrupy mass. By reducing proteinase activity in yeast cells, not only are fewer enzymes released into the dough upon cell lysis, but dough proof times are decreased by about 50% as compared to dough having a GSL yeast. It is believed that proteins involved in fermentation are not broken down as during normal cell regulation.

By "conventional yeast" is meant a yeast cell of the genus species Saccharomyces cerevisiae capable of metabolizing carbohydrates that include glucose, galactose, maltose and fructose. Activities of enzymes participating in the metabolism of carbohydrates other than glucose are reduced when the conventional yeast is grown in a media that contains glucose. One conventional yeast is baker's yeast.

A conventional galactose substrate limited (GSL) yeast refers to a galactose substrate limited yeast that is substantially unable to ferment galactose in the presence of glucose.

The yeast cell of the present invention is capable of utilizing a substrate of pure galactose as well as hydrolyzed lactose. As discussed, before the yeast cell of the present invention, many yeasts, including galactose substrate limited (GSL) yeast strains, were metabolically impaired when exposed to abundant amounts of glucose. As a consequence, the yeast strains were unable to effectively metabolize galactose present in a lactose-derived substrate, such as hydrolyzed lactose syrup. This deficiency is believed to be due to a glucose induced catabolite repression.

The metabolic impairment of the GAL-substrate limited yeast strains has been attributed to several factors. A first factor is a repression of the synthesis of catabolite enzymes and/or a proteolytic breakdown of catabolite enzymes. A second factor for metabolic impairment has been attributed to the disassembly of mitochondrial structures. A third factor is a combination of the first and second factors. The net effect of the metabolic impairment is that yeast cells have been unable to effectively convert sugar other than glucose to carbon dioxide until enough glucose has been metabolized so that the glucose concentration falls below some critical level.

Galactose substrate-limited yeast strains are unable to metabolize glucose. Thus, in the presence of glucose and glucose catabolites, GAL-substrate limited yeast strains stop metabolizing. That the GAL-substrate limited yeast strains of the present invention do not experience catabolite repression in the presence of glucose is then a great improvement over conventional GAL-substrate limited yeast.

The diploid yeast cells of the present invention are made by a process that includes steps of mating selected haploid yeast cells, creating conditions that promote spore formation of the yeast cells in yeast colonies, isolating yeast colonies, screening yeast samples from the yeast colonies for desired traits and growing selected colonies to make yeast strains, creating diploid yeast cells from the strains and evaluating the diploid yeast cells in a nutrient matrix, such as a bread dough. Typically, out of 700 haploid yeast candidates, two yeast strains are ultimately selected for evaluation in a nutrient matrix. In the present case, three yeast strains have been found to have excellent preservation of galactose substrate limited specificity and non-reversion.

A diploid yeast strain is preferable to a haploid strain in the present invention because the diploid strain is more robust due to a doubling of the amount of genetic material. Diploid yeast strains in general grow and evolve carbon dioxide more rapidly than haploid yeast strains. Complementation enhances preservation of genetic expression in diploid strains and causes them to be robust. Diploid strains are also more efficiently produced commercially and proof a bread dough more quickly than a haploid yeast strain.

The diploid yeast cell of the present invention is prepared as described in the following examples. These examples are presented in order to exemplify various embodiments of the present invention and are not intended to limit the present invention.

As used herein, strain D308.3 refers to a haploid galactose substrate-limited (GSL) strain of S. cerevisiae that has an adenine mutation with colonies that are pink in color. A strain, MSL.1, is a non-adenine requiring revertant of D308.3. Colonies of this strain are not pink. A strain, a/α GSL#33, is a diploid GSL strain. A strain GSL#33 is a haploid strain that is GSL. A strain, CAT-15, is a haploid GSL strain, that is catabolite non-repressed, and is able to ferment hydrolyzed lactose syrup. A strain, 10×54 is a diploid GSL strain that is catabolite non-repressed. The strains CAT-15 and 10×54 have an ability to proof dough that includes a hydrolyzed lactose substrate. The strains MSL .1 and a/α GSL#33 are unable to effectively ferment and grow on a hydrolyzed lactose syrup.

Strains D308.3 was deposited with the American Type Culture Collection, ATCC, in Rockville, Md. on Mar. 5, 1993, and has accession number 74211. This deposit was made in accordance with Budapest Treaty on the International Recognition of the Deposit of Microorganisms for the Purposes of Patent Procedure.

EXAMPLE I

Haploid yeast strains MSL.1 and a GSL#33 were grown on media containing glucose and galactose. As described, wild type yeast strains of MSL.1 and a GSL#33 could not metabolize lactose. Catabolite non-repressed haploid yeast strains were cultivated from these strains as described.

Materials required included the following yeast strains having the corresponding genotypes:

| Yeast Strains | Genotype |
|---|---|
| MSL.1 | hxk1 hxk2 glk1 trp1 his2 met14 |
| a GSL#33 | hxk1 hxk2 glk1 met14 his2 lys2* |

*Genotype based on growth behavior on various drop out media plates and genotype of parental strains.

A quantity of 50 mls of yeast extract peptone media (YEP) and galactose was poured into two autoclaved culture flasks. One flask was inoculated with an isolated colony of yeast strain, MSL.1, while the other flask was inoculated with an isolated colony of yeast strain, "a" GSL#33.

The inoculated cultures were placed into a 30° C. shaker incubator and incubated under agitation. The MSL.1 culture was incubated for 48 hours while the less vigorous "a" GSL#33 sample was incubated for 72 hours.

Subsequent to the incubation period, a quantity of 100 microliters of $10^{-1}$, $10^{-2}$, $10^{-3}$, and $10^{-4}$ dilutions of the aforementioned yeast cultures were spread plated onto 60% glucose/40% galactose YEP plates having an agar formula as follows:

60% Glucose/40% Galactose YEP AGAR
Bacto-yeast extract (1%) 10 gm
Bacto-peptone (2%) 20 gm
Glucose (1.2%) 12 gm
Galactose (0.8%) 8 gm
Bacto-agar (2%) 20 gm
Distilled water 1000 ml.

In addition, $10^{-5}$ through $10^{-8}$ dilutions of each culture were spread plated onto YEP media and galactose containing media, respectively. All plates were incubated at 30° C. Yeast colonies were counted. Titer results indicated that the MSL.1 culture had a cell density of about $1.3 \times 10^8$ CFU/ml while the density of the "a" GSL#33 was equal to about $6 \times 10^7$ CFU /ml.

Candidate catabolite non-repressed (CAT-) revertant colonies grew vigorously on the 60% glucose/40% galactose plates while the metabolically impaired "wild" type control colonies appeared as an indistinguishable thin film.

After approximately 5 days incubation at 30° C., a total of 82 potential MSL.1 and 68 "a" GSL#33 CAT- colonies were isolated from the 60% glucose/40% galactose YEP selection plates. In order to separate revertant colonies that were no longer galactose substrate limited from colonies which were galactose substrate limited but not catabolite repressed, all candidate CAT- GSL strains were grid plated onto plates containing yeast extract galactose YEP media. The plates were stored at 30° C. for approximately one week.

Of the 68 "a" GSL#33 CAT- candidates plated, 43 grew on the 60% glucose/40% galactose YEP plates but were unable to grow on the YEPD plates. These yeast colonies appeared to be CAT- GSL yeast strains. The remaining 24 colonies grew readily on YEPD and no longer appeared to be galactose substrate limiting.

None of the candidate MSL.1 CAT- colonies proved to be CAT-. All candidates tested grew equally well on 60% glucose/40% galactose and YEPD media.

The 43 CAT- GSL candidates were tested for liquid media carbohydrate utilization. The degree of non-repression of the putative CAT- GSL colonies isolated, the ability of the colonies to grow in liquid YEP without sugar, YEPD media, YEPD and galactose media, and YEP and 50% glucose/50% galactose liquid media were also evaluated.

Test tube samples containing 10 mls of YEP and galactose were inoculated with an isolated colony of candidate CAT-GSL yeast paste. The samples were then incubated in a shaker incubator at 30° C. under agitation for about 24 hours. Control "GSL#33 and GSL#33" α/A samples were also prepared in the YEP and galactose media.

Subsequent to the incubation period, test tube samples containing 10 mls of YEP media without sugar, YEPD media, YEP and galactose media and YEP and 50% glucose/50% galactose media were inoculated with 100 microliters of a log phase starter culture of each strain evaluated. Subsequent to inoculation, absorbance measurements were taken for each sample at 600 nanometers, nm, in an optical spectrophotometer prior to placing the samples into a 30° C. incubator. Absorbance measurements were recorded over a nine day period of time in order to quantify yeast growth.

Approximately 24 of the 43 CAT- GSL candidates evaluated appeared to grow more quickly and vigorously on the 50% glucose/50% galactose liquid media than either of the diploid control a GSL#33 or haploid MSL.1 parental GSL strains. The 24 candidates were identified as follows: CAT-GSL#1, 2, 3, 4, 6, 7, 8, 9, 10, 12, 15, 16, 17, 18, 19, 20, 24, 26, 27, 35, 36, 37, 40 and 41. Another two candidates, 23 and 25 also displayed superior growth performance. Growth rates for these strains are shown in FIGS. 2–7. The rates were rounded to the nearest 0.025 mls of gas evolution per minute. The plots are shown in FIGS. 2 to 7.

These candidates were screened for performance in bread dough. The screening tests included Risograph gas evolution tests to evaluate an ability of each yeast strain to leaven and proof bread dough. Risograph gas evolution from bread dough leavened and proofed with the candidate yeast strains and dough product proof time experiments indicated that many of the CAT- GSL yeast strains evolved carbon dioxide at a faster rate and produced significantly more total carbon dioxide than either diploid control yeast or parental haploid GSL yeast strains. That the CAT- GSL yeast strains effectively metabolized galactose in the presence of glucose was of particular importance in proofing GSL yeast leavened dough products employing a food grade hydrolyzed lactose syrup.

The 26 yeast colonies identified above were screened for performance in leavening and proofing bread dough. The following Table 1 summarizes data of proof time, gas evolution rate, total gas evolution and cell yield of bread dough made with the candidate yeast stains. Table 1 indicates 5–7 strains in each category that outperformed other candidates in the screening test and outperformed the control, a/α GSL#33.

TABLE 1

| Preferred Strains (in descending order) | Proof Time (hr) | Gas Evolution Rate (ml/min) | Total Gas Evolution (ml) | Yield (g/l) | |
|---|---|---|---|---|---|
| #1 | Cat 10 3.1 | Cat 15 0.150 | Cat 37 90 | a/α GSL#33 24.0 | |
| #2 | Cat 15 3.5 | Cat 37 0.150 | Cat 20 85 | Cat 37 | 19.9 |
| #3 | Cat 1 4.2 | Cat 25 0.125 | Cat 2 77 | Cat 20 | 19.2 |
| #4 | Cat 37 4.3 | Cat 24 0.125 | Cat 16 72 | Cat 25 | 19.0 |
| #5 | Cat 40 4.4 | Cat 23 0.125 | Cat 15 72 | Cat 4 | 19.0 |
| #6 | | Cat 2 0.125 | Cat 36 72 | Cat 18 | 19.0 |
| #7 | | Cat 12 0.125 | | | |
| a/α GSL#33 | 6.6 | 0.050 | 50 | 24 | |
| Preferred Range | 3.1–6.6 | 0.150–0.050 | 90–50 | 24–19 | |
| Average | 3.9 | 0.132 | 78 | 19.2 | |

Table 2 indicates a frequency at which each candidate strain appeared on the most preferred performers table as described in Table 1. The letters represent proof time, gas evolution rate, total gas evolution and yield.

TABLE 2

| Strain | P | R | T | Y |
|---|---|---|---|---|
| 1 | P | | | |
| 2 | | R | T | Y |
| 4 | | | | Y |
| 10 | P | | | |
| 12 | | R | | Y |
| 15 | P | R | T | |
| 16 | | | T | |
| 18 | | | | Y |
| 20 | | | T | Y |
| 23 | | R | | |
| 24 | | R | | |
| 25 | | R | | Y |
| 36 | | | T | |
| 37 | P | R | T | Y |
| 40 | P | | | |
| a/α GSL33 | | | | Y |

As demonstrated in Tables 1 and 2, several strains were superior in more than one criteria. CAT- 37 made all four criteria, and CAT- 2 and CAT-15 were successful in 3 criteria. Of these criteria, proof time was the most important in determining performance of bread dough. CAT- 10 was superior only in proof time. Several of the strains on this list were later used in mating protocols to create a catabolite non-repressed, GSL, diploid yeast strain.

FIG. 1 is a bar graph showing the dough proof times of all strains tested. The control strain, a/α GSL#33, had the longest proof time at 6.6 hours. That all candidates outperformed the control strain indicates that these candidates were indeed catabolite non-repressed. The candidates having the shortest proof times were CAT- 10, CAT-15, CAT- 1, CAT- 37 and CAT- 40. CAT- 10 and CAT-15 proof times were about half as long as the control yeast.

Candidates were also tested for carbon dioxide production. Candidates were blended with ingredients of flour and water to make a bread dough. CAT-15 and CAT- 37 had the highest carbon dioxide production rates of all strains considered. The strains, CAT- 25, CAT- 24, CAT- 23, CAT- 2 and CAT- 12 had carbon dioxide production rates slightly below rates of the strains CAT-15 and CAT- 37.

The most preferred candidates in total gas evolution in bread dough did not always match those candidates with the best carbon dioxide rates. Of the top six total $CO_2$ producers, only CAT- 37, CAT- 2 and CAT-15 also had superior $CO_2$ evolution rates.

The gas evolution of the CAT- strains in bread dough was substantially lower than the total gas and rate generated by conventional baker's yeast. This is a desirable feature of a yeast strain used in making a refrigeratable bread dough. It permits the yeast strain to be used to leaven and proof the dough in a container without rupturing containers storing the dough.

With respect to cell yield, all CAT- candidates had lower yields than the a/α GSL#33 control strain. This is believed to be due to the a/α GSL#33 being a diploid strain and all other strains tested being haploid strains. Because diploid strains have two copies of the genetic information rather than one, the a/α GSL#33 yeast cells were able to grow more rapidly. Complementation of auxotrophic markers enhanced the growth rate of the diploid control relative to the haploid strains. Of the haploid strains, there were several strains that were very close to 20 grams per liter. This was a generally high yield.

EXAMPLE II

A proteinase deficient mutation was introduced into a galactose substrate limited (GSL) yeast strain. A proteinase deficient yeast strain, α pep 4-3, was successfully mated to a haploid GSL yeast strain, a GSL#33 CAT- 10, described in Example 1. A heterozygous diploid colony obtained from this mating was plated onto a sporulation media. Haploid spore generated colonies were isolated. The haploid colonies were screened for the galactose substrate limitation, that is, growth on galactose but not glucose, and catabolite non-repression, that is, an ability to grow in the presence of glucose.

A total of 73 haploid GSL catabolite non-repressed (CAT-) candidates were isolated. The haploid candidates were screened for the pep 4-3 mutation. Assays for proteinase A activity and a second assay for proteinase B activity were used to screen the haploid candidates.

Haploid strains GSL/CAT- PEP 4-3 (CAT 39 No. 6); 10×4–3 (#54) and 15×8 (#10) were received by the American Type Culture Collection, ATCC, in Rockville, Md., in accordance with the Budapest Treaty on the International Recognition of the Deposit of Microorganisms for the Purposes of Patent Procedure on Nov. 8, 1994 and have accession numbers 74306, 74307, 74309 respectively.

EXAMPLE III

In the isolation of GSL/CAT- haploid yeast candidates to create a diploid GSL/CAT- yeast strain, a yeast strain possessing a low temperature sensitive mutation, lts 8, was employed to introduce an α mating type gene into the GSL haploid candidate pool. A total of 36 haploid GSL/CAT- candidates strains were isolated. Ten of the haploid strains appeared to be low temperature sensitive as well. The suitable yeast strains possessing a low temperature sensitive mutant have been deposited with the American Type Culture Collection, ATCC, of Rockville, Md., in accordance with the Budapest treaty on the International Recognition of the deposit of Microorganisms for the Purposes of Patent Procedure. The strains have ATCC accession numbers and identification numbers in parenthesis as follows: 74219 (cdc 19), 74124 (XA6-9C-lts1), 74125 (AXC-94B-lts2), 74126 (XA77-34B-lts3), 74127 (XA99-13C-lts4), 74128 (XA98-3D-lts5), 74129 (XA88-3A-lts6), 74130 (XA89-2A-lts7), and 74131 (XA33-5A-lts8) deposited Jan. 31, 1992.

EXAMPLE IV

Bread doughs made with conventional baker's yeast cultures, typically have at least 2% ethanol added to the dough to inhibit lactic acid bacterial growth, stabilize dough can pressure, and minimize rheological shelf life changes in dough. Unfortunately, ethanol also inhibits yeast growth and gas production. A GSL strain was isolated for refrigeratable dough applications that displays ethanol tolerance.

The isolation occurred by performing successive isolation and re-inoculation steps of viable yeast colonies obtained from stationary phase cultures grown in a presence of 6% ethanol. The isolation was based on a premise that the more ethanol tolerant an isolated colony, the faster the colony would grow in the presence of ethanol.

Two promising ethanol tolerant candidates were isolated and tested in refrigerated dough systems. The results indicated that the ethanol tolerant colonies were able to proof dough samples more quickly than a parent 10×54 yeast strain, described in Example 5. Proof times were reduced by one-half to one hour. One of the ethanol tolerant colonies, E35#1, as been deposited with the American Type Culture Collection, in Rockville, Md. in accordance with the Budapest Treaty on the International Recognition of the Deposit of Microorganisms for the Purposes of Patent Procedure. The E35#1 strain was received by the ATCC on Nov. 8, 1994 and has accession number 74310.

EXAMPLE V

To create the most metabolically robust GSL/CAT- diploid yeast strain possible, a screen of putative haploid GSL/CAT- yeast strains isolated to grow on YEP (no sugar) media, YEPD media, YEP plus galactose media, and a 50/50 molar percent galactose/glucose YEP liquid media was performed. Haploid yeast strains found to grow most readily on the 50/50 galactose/glucose media were mated to create diploid GSL/CAT- yeast strains. The ability of the candidate diploid GSL/CAT- strains to evolve carbon dioxide and proof a refrigeratable dough was evaluated. The most efficient strains were further analyzed.

The efficient haploid strains included the following:

a GSL33 CAT- (a.k.a. 33)#: 1, 2, 3, 4, 6, 7, 8, 9, 10, 12, 15, 16, 17, 18, 19, 20, 24, 25, 27, 29, 31, 32, 33, 35, 36, 39, 40, 41 a GSL33 CAT-15×alts 8 (a.k.a 15×8) #: 1, 2, 3, 4, 7, 8, 9, 10, 12, 15, 16, 17, 18, 19, 22, 23 a GSL33 CAT-10×pep4-3 (a.k.a. 10×4-3)#: 1–74

Of the yeast strains evaluated, only 13 were found to retain the GSL/CAT- phenotype and possess auxotrophic markers suitable for mating via complementation. The phenotype screened included these features: i. the yeast grew readily in YEP+Gal media; ii. grew readily in YEP+50% gal/50% glucose media; iii. did not grow readily in YEP+ dextrose media—when compared to an observed growth rate in a YEP (no sugar) control media.

Based on compatible mating type and complimentary auxotrophic marker combinations, the following yeast strain mating pairs, listed in Table 3 were identified. Also listed is a minimal selection media based upon auxotrophic markers of the yeast strains.

TABLE 3

| α mating strain | a mating strain | Syn. Gal Minimal Selection Media* |
|---|---|---|
| 15×8 #10 | 10x4-3 #54 | no supplementation |
| " | 10x4-3 #58 | no supplementation |
| 10x4-3 #5 | CAT33 #15 | lysine |
| " | CAT33 #20 | lysine |
| " | CAT33 #25 | lysine |
| " | CAT33 #27 | lysine |
| " | 10x4-3 #52 | lysine |
| " | 10x4-3 #54 | no supplementation |
| " | 10x4-3 #58 | no supplementation |
| " | 10x4-3 #71 | lysine |
| 10x4-3 #57 | 10x4-3 #51 | no supplementation |
| 10x4-3 #59 | CAT33 #15 | lysine |
| " | CAT33 #20 | lysine |
| " | CAT33 #25 | lysine |
| " | CAT33 #27 | lysine |
| " | 10x4-3 #52 | lysine |
| " | 10x4-3 #54 | no supplementation |
| " | 10x4-3 #58 | no supplementation |
| " | 10x4-3 #71 | lysine |

*The selection media employed was synthetic galactose minimal media plus lysine supplementation when both parent strains required lysine for growth.

The haploid mating yeast strain pairs listed in Table 3 were line plated onto YEP+Gal media and incubated at 30° C. for 24 hours. The line plates were then cross-replica plated onto YEP+Gal in a perpendicular orientation and incubated at 30° C. for 24 hours. The cross-replica plates were then replica plated onto synthetic galactose minimal media, with or without lysine supplementation. The plates were incubated for 1–4 days at 30° C. Diploid yeast colony growth was evident for the mating pair combinations listed as "+".

TABLE 4

| α mating strain | a mating strain | Diploid Yeast Colony Growth* |
|---|---|---|
| 15×8 #10 | 10x4-3 #54 | + |
| " | 10x4-3 #58 | + |
| 10x4-3 #5 | CAT33 #15 | − |
| " | CAT33 #20 | − |
| " | CAT33 #25 | − |
| " | CAT33 #27 | − |
| " | 10x4-3 #52 | + |
| " | 10x4-3 #54 | + |
| " | 10x4-3 #58 | + |
| " | 10x4-3 #71 | + |
| 10x4-3 #57 | 10x4-3 #51 | + |
| 10x4-3 #59 | CAT33 #15 | − |
| " | CAT33 #20 | − |
| " | CAT33 #25 | − |
| " | CAT33 #27 | − |
| " | 10x4-3 #52 | + |
| " | 10x4-3 #54 | + |
| " | 10x4-3 #58 | + |
| " | 10x4-3 #71 | + |

*Diploid colony growth was observed on the synthetic galactose minimal media plate (+/− lysine) where the two haploid strains overlapped one another.

The putative diploid GSL/CAT- colonies listed in Table 4 were further isolated by plating onto fresh synthetic galactose minimal media with or without lysine followed by plating isolated colonies onto fresh YEP+galactose plates.

The ability of the putative diploid GSL/CAT- yeast strain to utilize galactose and/or glucose was evaluated by spread plating a heavy inoculum of 100 microliters of a one loop yeast paste in 3 milliliters, mls, of dilution buffer onto YEP media and galactose and YEPD media plates. A haploid GSL/CAT- yeast strain sample, CAT-15, was prepared as a control. The plates were stored at 30° C. for approximately four days. All the candidate diploid yeast strains evaluated grew readily on YEP and galactose media and showed no signs of growth, or few revertant colonies, on the YEPD media plates.

Figure 8:
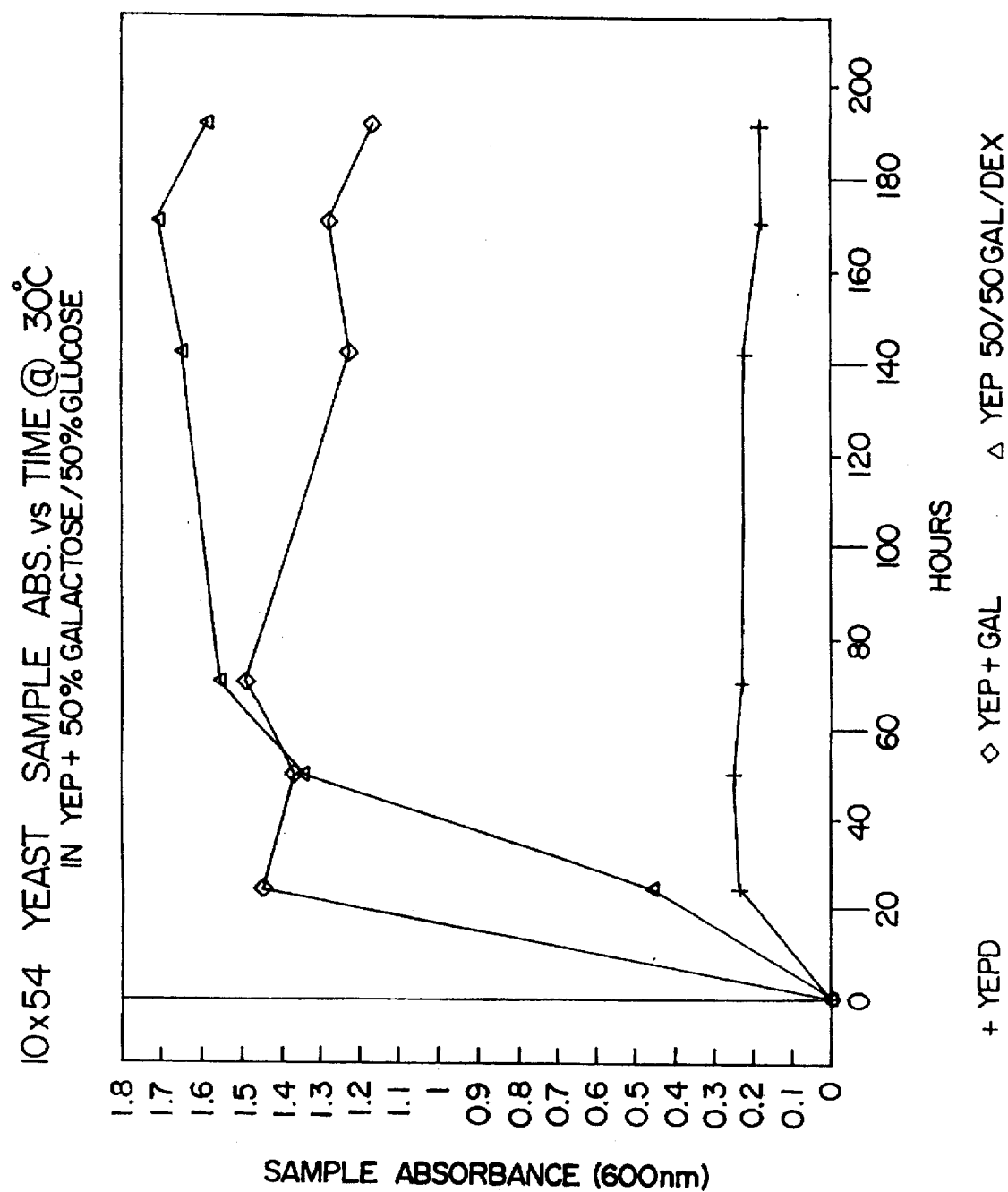
FIG. 8 graphically shows growth rates of a diploid 10×54 yeast on three types of growth media as measured by absorbance at 600 nm of a culture of each yeast strain.

Based on the observations above, it was concluded that the isolated diploid GSL/CAT- yeast strains were galactose substrate limited. The strains were also screened for a capacity to metabolize other carbohydrates, growth in liquid YEP media, YEPD media, YEP+galactose media and YEP+ 50% glucose/50% galactose media, and for a capacity to leaven and proof bread dough samples within 8 hours. Three of the putative diploid strains, 5×54, 59×58 and 10×54, performed acceptably on all of the screening tests. Growth for the 10×54 strain is graphically shown in FIG. 8.

Strain 10×54 has been received by the ATCC in Rockville, Md., in accordance with the Budapest Treaty on the International Recognition of the Deposit of Microorganisms for the Purposes of Patent Procedure on Nov. 8, 1994, and has accession number 74308.

These three strains were tested for reversion to glucose utilization by inoculating the yeast strains on a media of YEP+galactose. Results are shown in Table 5.

TABLE 5

| Strain | Reversion Frequency |
|---|---|
| CAT-15 | $10/5.2 \times 10^7 = 1.92 \times 10^{-7}$ 1.92 revertants in $10^7$ cells |
| 5x54 | $30/2.04 \times 10^8 = 1.47 \times 10^{-7}$ 1.47 revertants in $10^7$ cells |
| 10x54 | $45/1.65 \times 10^8 = 2.73 \times 10^{-7}$ 2.73 revertants in $10^7$ cells |
| 59x58 | $470/6.2 \times 10^7 = 7.58 \times 10^{-6}$ 7.58 revertants in $10^6$ cells |

The observed reversion frequencies calculated above are representative of reversion frequencies observed for point mutations.

The three diploid strains were also screened for auxotrophic nutritional requirements. The strains were plated onto a synthetic galactose minimal growth media. All of the strains were able to grow on the minimal media.

It has been found that yeast strains of the present invention, when incorporated in a bread dough, produced a yeast leavened and yeast proofed refrigeratable dough. Bread baked from the dough of the present invention compares favorably with bread made from a conventional baker's yeast.

Although the present invention has been described with reference to preferred embodiments, workers skilled in the art will recognize that changes may be made in form and detail without departing from the spirit and scope of the invention.

What is claimed is:

1. A method for converting whey to glucose and ethanol comprising:

providing a yeast cell of a genus species *Saccharomyces cerevisiae* strain selected from one or more of ATCC No. 74306, 74307, 74308 and 74309 solely utilizing galactose as a carbohydrate source in the presence of glucose;

interspersing the yeast cell into whey; and extracting glucose and ethanol produced by the action of the yeast cell on the whey.

2. The method of claim 1, wherein a lactose fraction of the whey is hydrolyzed to glucose and galactose.

3. A method for converting whey to ethanol comprising:

providing a yeast cell of the genus species *Saccharomyces cerevisiae* strain ATCC No. 74310 utilizing solely galactose as a carbohydrate source and a yeast cell capable of utilizing glucose;

interspersing the yeast cells into whey; and extracting ethanol produced by the action of the yeast cells on the whey.

4. The method of claim 3, wherein a lactose fraction of the whey is hydrolyzed to glucose and galactose.

* * * * *

UNITED STATES PATENT AND TRADEMARK OFFICE
CERTIFICATE OF CORRECTION

PATENT NO. : 5,744,330
DATED : April 28, 1998
INVENTOR(S) : David J. Domingues

It is certified that error appears in the above-indentified patent and that said Letters Patent is hereby corrected as shown below:

Col. 5, line 64, between the words "extract" and "galactose" insert --peptone media with dextrose (YEPD media) and 60% glucose/40%--.

Col. 6, line 64, delete the word "stain" and insert --strains--.

Col. 7, line 23, delete the word "proof" and insert --"proof"--.

Col. 9, line 52, delete "a GSL33 CAT-" after the number "23".

Col. 9, line 53, before the word "10xpep4-3" insert "a GSL33 CAT-".

Signed and Sealed this

Twenty-fifth Day of August, 1998

Attest:

BRUCE LEHMAN

*Attesting Officer*   *Commissioner of Patents and Trademarks*